United States Patent [19]
Devonec

[11] Patent Number: 5,766,209
[45] Date of Patent: Jun. 16, 1998

[54] PROSTHESIS INTENDED FOR THE TREATMENT OF A NATURAL LUMEN OR TRACT, IN PARTICULAR AN ENDO-URETHRAL PROSTHESIS

[76] Inventor: Marian A. Devonec, 81 avenue des Balmes, 01700 Miribel, France

[21] Appl. No.: 501,140

[22] PCT Filed: Feb. 16, 1994

[86] PCT No.: PCT/FR94/00171

§ 371 Date: Aug. 15, 1995

§ 102(e) Date: Aug. 15, 1995

[87] PCT Pub. No.: WO94/18907

PCT Pub. Date: Sep. 1, 1994

[30] Foreign Application Priority Data

Feb. 19, 1993 [FR] France ................................. 93 02284

[51] Int. Cl.[6] .................................................. A61M 25/00
[52] U.S. Cl. .................................. 604/8; 604/9; 623/12
[58] Field of Search .................................. 623/11, 12, 1; 604/8–9, 93, 164, 212; 606/108–191, 153, 198

[56] References Cited

U.S. PATENT DOCUMENTS

| | | | |
|---|---|---|---|
| 3,527,226 | 9/1970 | Hakim | 604/9 |
| 3,657,744 | 4/1972 | Ersek . | |
| 3,938,529 | 2/1976 | Gibbons | 604/8 |
| 4,240,434 | 12/1980 | Newkirk | 604/9 |
| 4,423,725 | 1/1984 | Baran et al. . | |
| 4,973,301 | 11/1990 | Nissenkorn . | |
| 5,059,169 | 10/1991 | Zilber | 604/8 |
| 5,078,720 | 1/1992 | Burton et al. . | |
| 5,122,154 | 6/1992 | Rhodes . | |
| 5,176,625 | 1/1993 | Brisson | 604/8 |
| 5,282,784 | 2/1994 | Willard | 604/8 |

FOREIGN PATENT DOCUMENTS

| | | |
|---|---|---|
| 0 341 988 B1 | 11/1989 | European Pat. Off. . |
| 2 667 783 | 4/1992 | France . |
| WO 91/16005 | 10/1991 | WIPO . |

OTHER PUBLICATIONS

The Titan Intra-Prostatic Stent, Advanced Surgical Intervention, Inc. Not Dated.
UltraFlex Urethral Stent System, Microvasive Boston Scientific Corporation. Not Dated.
Memothem Ureteral Stents, angiomed. Not Dated.
Intraurethral Katheter, angiomed. Not Dated.
Barnes Stent, Bard. Not Dated.

(List continued on next page.)

*Primary Examiner*—John G. Weiss
*Assistant Examiner*—Bruce E. Snow
*Attorney, Agent, or Firm*—Oliff & Berridge, PLC

[57] ABSTRACT

Prosthesis (8) intended for the treatment of a natural lumen (1) or tract of a human or animal body through which a flow is effected on either side of a sphincter (5), said prosthesis comprising a tubular element (9, 11), in particular of cylindrical shape, which is sufficiently flexible to conform to said natural lumen, but sufficiently rigid to maintain an artificial passage in said lumen, and is intended to be placed in said natural lumen, the wall of said tube comprising a relatively smooth and soft biocompatible material, such as a silicone rubber, at least in its outer part, characterized in that said prosthesis comprises two tubular elements (9, 11), such as are defined in the preamble of the present claim, which are intended to be arranged in said lumen (1) on either side, respectively, of the sphincter (5), and are attached to each other by a flexible and deformable connection means (10) which is intended to be held in the orifice of the sphincter (5), and each said tubular element having an external cross section which is substantially constant from one end to the other of said element.

22 Claims, 6 Drawing Sheets

OTHER PUBLICATIONS

Urocoil, Prostacoil, Almed. Not Dated.
Prostakath, Pharma–Plast A/S. Not Dated.
Variospire, Laboratoires Bruneau. Not Dated.
Uromed, Urologische Spirale, Uromedical–Products. Not Dated.
La Spirale, Porges. Not Dated.

R. Robert De Nicola, "Permanent Artificial (Silicone) Urethra," The Journal of Urology, vol. 63, No. 1, Jan. 1950, pp. 168–172.

L.A. Loizou, M.D., et al., "Treatment of malignant strictures of the cervical esophagus by endoscopic intubation using modified endoprostheses," Gastrointestinal Endoscopy, 1992, pp. 158–164.

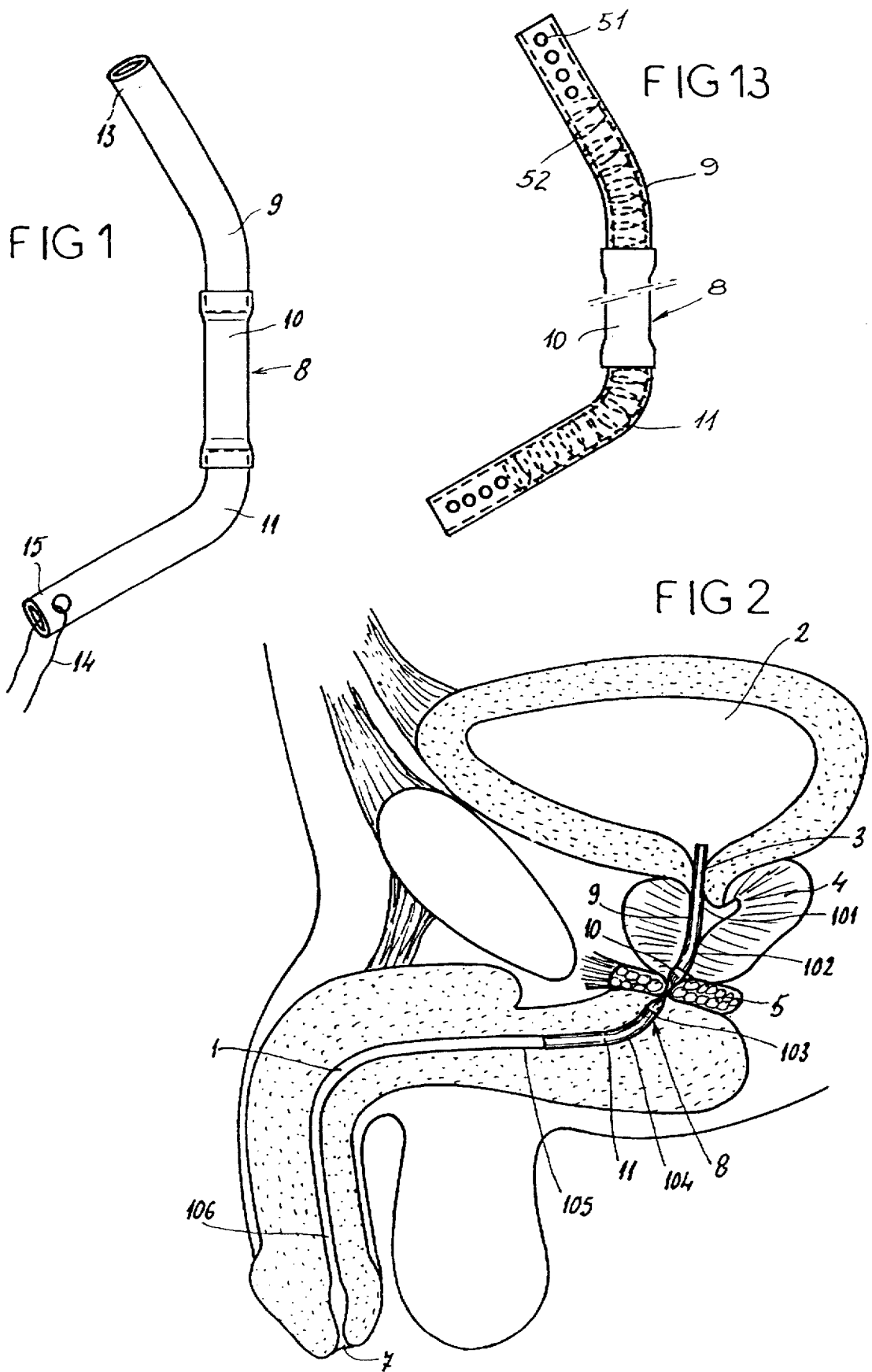

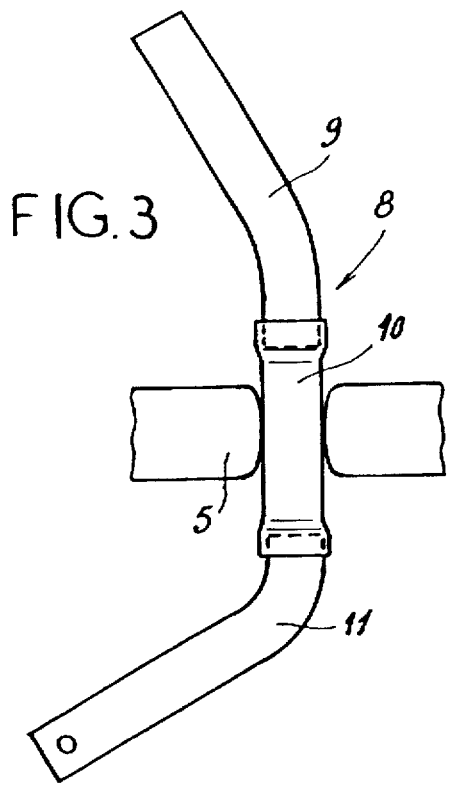
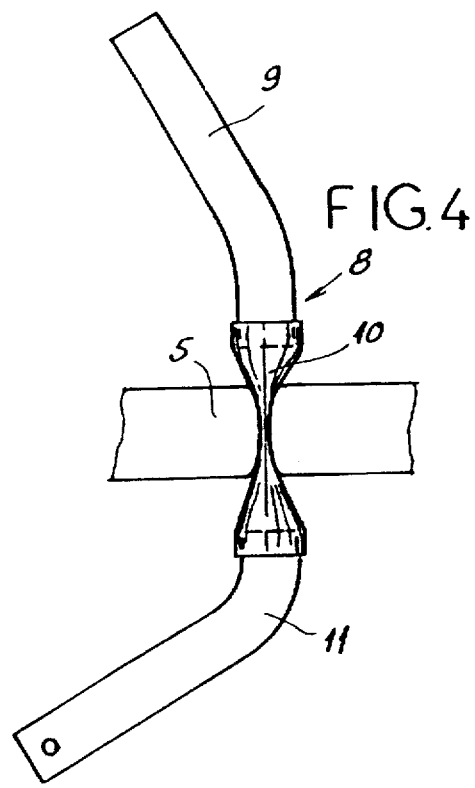
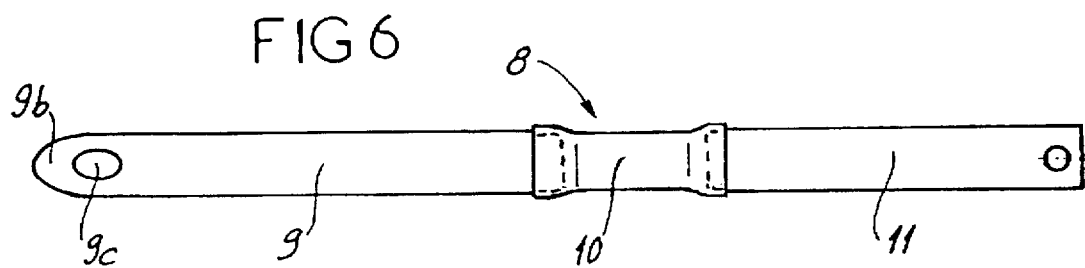
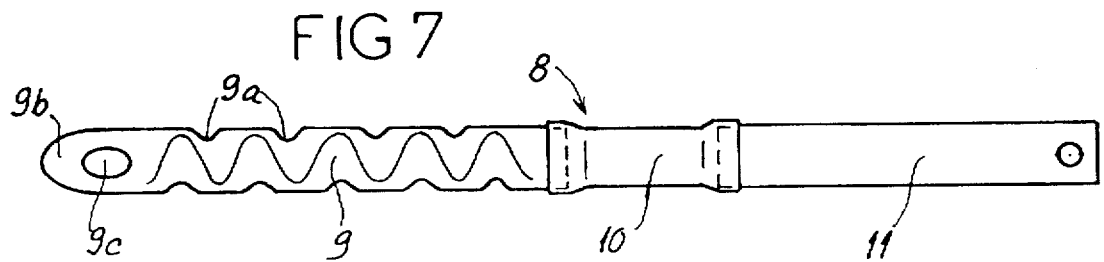

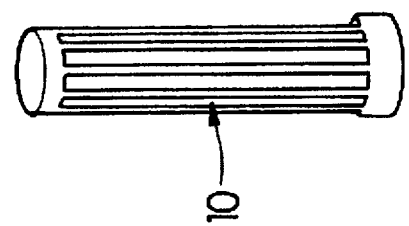
FIG. 5c
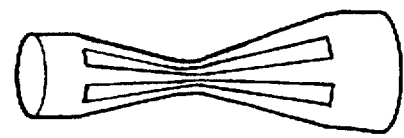
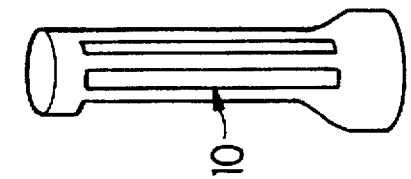
FIG. 5b
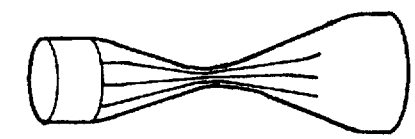
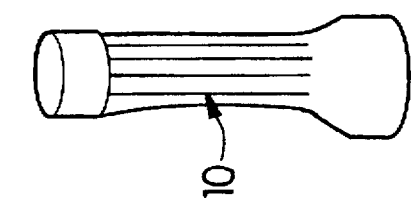
FIG. 5a

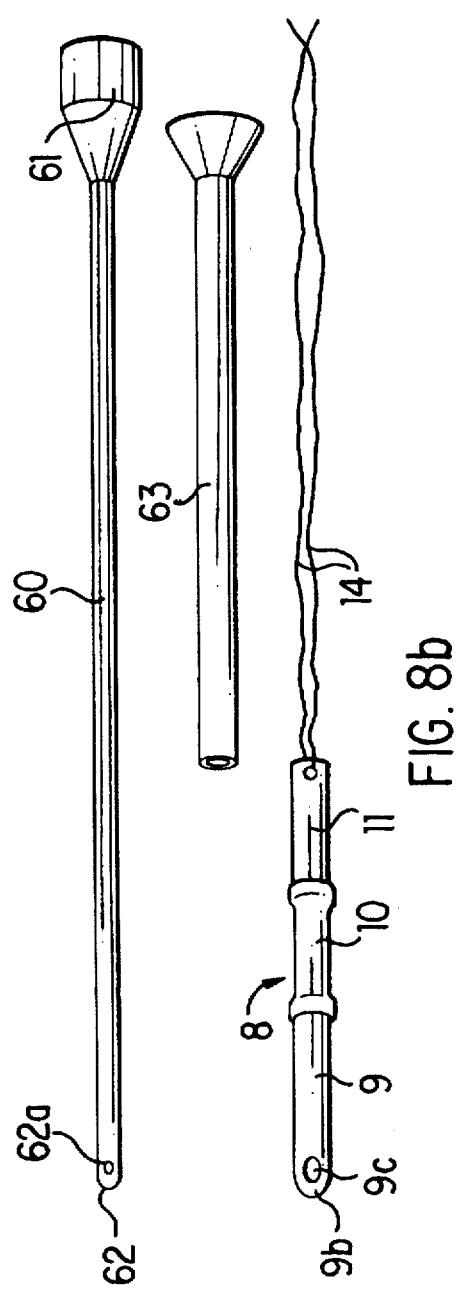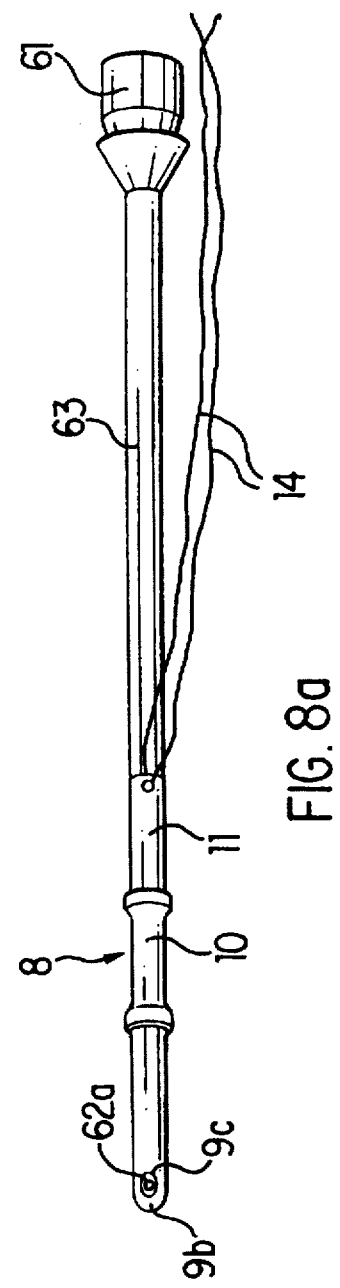
FIG. 8b
FIG. 8a

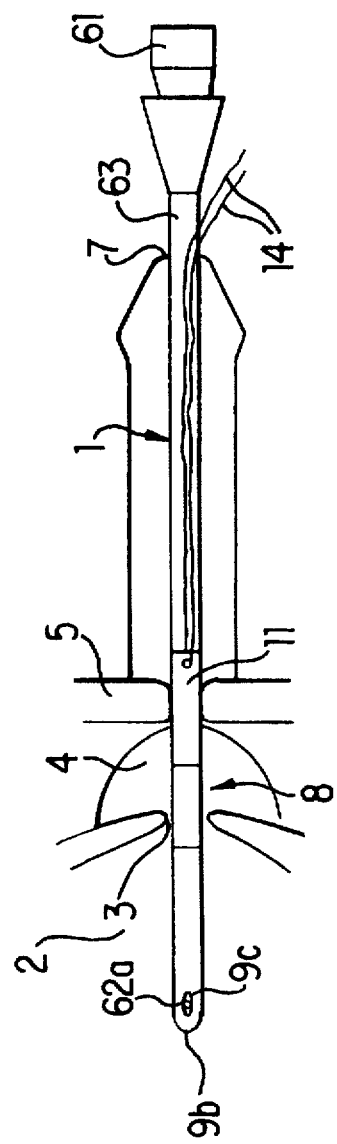
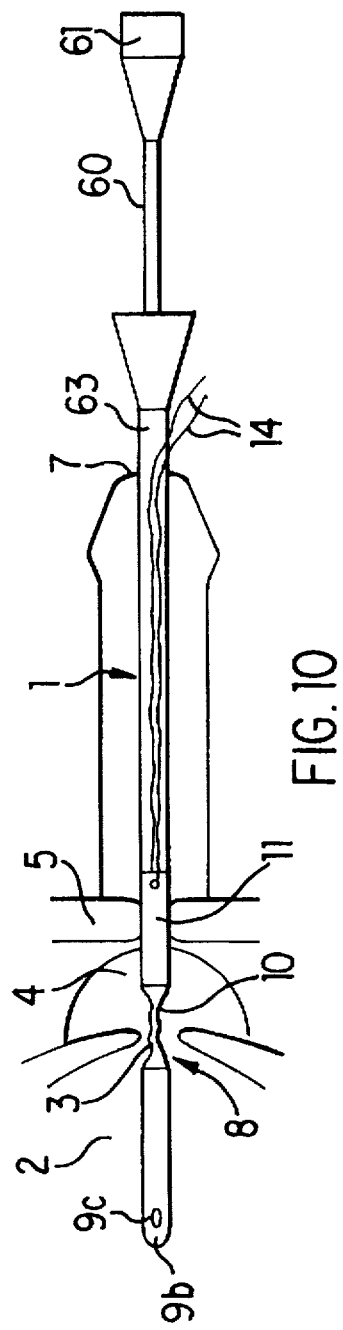

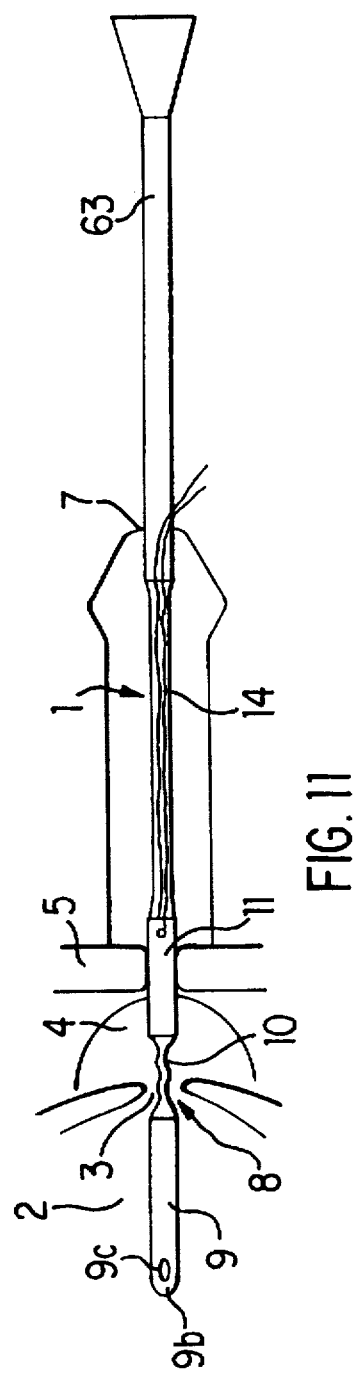
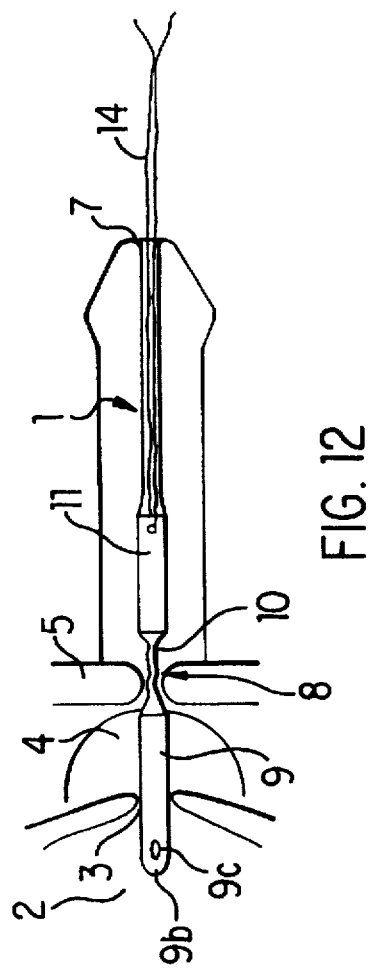

PROSTHESIS INTENDED FOR THE TREATMENT OF A NATURAL LUMEN OR TRACT, IN PARTICULAR AN ENDO-URETHRAL PROSTHESIS

BACKGROUND OF THE INVENTION

The present invention relates to the treatment of natural lumina or tracts of the human or animal body through which a transit or flow of a fluid is effected, in particular a body fluid, either liquid or gaseous, on either side of a sphincter. The urinary, respiratory, digestive and gynecological tracts constitute natural lumina within the meaning of the present invention.

"Treatment" is understood to mean both an intervention of a mechanical type, aiming to re-establish a flow which has previously been disturbed or prevented on account of an obstruction or a stenosis of the natural lumen, and also a treatment or intervention with a therapeutic objective, for example to control the cicatrization of the wall of the natural lumen after surgical intervention, or to reduce hyperplasia of an organ or gland surrounding this same lumen.

The present invention will be introduced, defined and described, by way of a non-limiting example, with reference to the endo-urethral prostheses which are used in the urethra in connection with the striated muscular sphincter.

In accordance with the document FR-A-2 667 783, an endo-urethral prosthesis has been described which consists of a tubular element, of general cylindrical shape, whose wall comprises a relatively smooth and soft biocompatible material, for example a silicone rubber, at least in its outer part. This tubular element is sufficiently flexible to conform to the anatomical profile of the urethra and to its movements, but sufficiently rigid, particularly in the radial or diametral direction, to maintain an artificial passage in the urethra. This tubular element is intended to be placed in the urethra, without passing through the striated muscular sphincter, in the prostatic segment and/or in any one of the membranous, bulbar, perineal and penile segments.

"Tubular element"[<b]old0 is understood to mean any element whose outer surface is described by a generatrix corresponding to a straight or curved line, or other line, about an axis.

According to the document FR-A-2 667 783, the tubular element is supported in the urethra principally by the elastic bearing of the wall of said element, in radial extension, against the urethral wall, and secondarily by various notches formed in the wall of the same tubular element, freeing catches which fasten on the urethral wall, somewhat in the manner of scales.

In practice, such a prosthesis is not self-stabilizing, for various reasons:

the elastic bearing of the tubular element is insufficient to support it in position in the urethra, except by providing or obtaining a very substantial bearing which is likely to damage the urethral wall, leading to the patient experiencing pains, and in any case rendering the withdrawal of the implanted prosthesis difficult or impossible, the fastening catches, or scales, cooperate with the urethral wall, in its longitudinal direction, only in the sense of precluding or limiting the descent of the prosthesis; these fastening catches cannot therefore prevent the prosthesis from ascending, the externally smooth nature of the tubular element encourages its natural sliding against the urethral wall, in particular during the various movements of the urethra, and, finally, the various notches constitute as many punctiform bearing surfaces, or zones of turbulence, on which both the static pressure and the dynamic pressure of the urinary flow act during miction; this has the result of encouraging the descent of the urethral prosthesis.

In accordance with the document WO91/16005, metal prostheses are furthermore known which consist of two elements, each consisting of metal coils, either contiguous or non-contiguous, which are intended to be arranged in the urethra on either side, respectively, of the striated muscular sphincter. For each element, these coils, which are compressible in a centripetal manner and are expansible in a centrifugal manner, define, in their expanded position, an enveloping surface with a cross section varying from one end to the other.

Prostheses are also known which consist of a metallic or non-metallic tube which is open-worked and is expansible at the moment of its implantation in the urethra.

At present, the various urethral prostheses proposed and described have been unable to reconcile:

on the one hand, the self-stabilizing which presupposes in one way or another, in the previous solutions, a certain anchoring of the prosthesis on the mucosa of the urethral wall, and, on the other hand, ease of introduction and especially of withdrawal of the prosthesis, that is to say its reversibility.

SUMMARY OF THE INVENTION

The present invention relates to a prosthesis, and in particular an endo-urethral prosthesis, which is self-stabilizing and which can be introduced and withdrawn in a non-traumatic manner from the natural lumen or tract in which it is implanted.

A prosthesis according to the invention comprises two tubular elements which are made from a relatively smooth and soft biocompatible material, such as a silicone rubber, and which are intended to be arranged in the lumen on either side, respectively, of the sphincter, and to be attached to each other by a flexible and deformable connection means which is intended to be held in the orifice of the sphincter. Each element has an external cross section which is substantially constant from one end to the other of said element.

This connection means preferably consists of a flexible sleeve, the two ends of which are connected, in continuity of flow, to the two tubular elements respectively; this connection means can also be a single connecting wire or several connecting wires which are attached individually at their two ends to the two tubular elements, respectively.

A prosthesis which comprises the technical characteristics defined hereinabove moreover affords the following decisive advantages.

The flexible sleeve or connection means constitutes a predetermined zone of bending of the prosthesis, which is capable of absorbing without stiffness all the movements of the natural lumen. This predetermined zone of bending permits harmonious functioning of the sphincter. The length of this flexible sleeve is moreover adapted to that of the sphincter.

Such a prosthesis has a uniform external profile, which fact renders it non-traumatic, both during its insertion and its removal, which maneuvers can be carried out without general anesthesia, and which fact makes it easy to position. This also makes it biocompatible in the sense that it does not irritate the inner mucosa of the natural lumen or tract.

Such a prosthesis also has an inner surface which is continuous and uniform, in particular as regards its internal cross section, which fact confers upon it very good hydraulic properties, that is to say without obstacle, for example, vis-a-vis urinary flow. As far as miction is concerned, a urethral prosthesis according to the invention is not moved by the urinary flow.

Such a prosthesis is self-stabilizing with respect to the sphincter: at rest, the sphincter immobilizes it, and during miction its sliding is prevented by the two tubular elements which are in abutment, respectively, on either side of the sphincter.

Such a prosthesis is also particularly easy to put into place, using simple instruments, in particular without necessarily having recourse to endoscopic or radiological checks. In particular, as is explained hereinafter, by simply sliding the endo-urethral prosthesis along the urethra, it is immobilized automatically in the correct position at the moment when the flexible sleeve arrives at the level of the sphincter which closes over it.

Essentially, such a prosthesis does not impede or disturb the functions of the sphincter; it opens and closes, and thus functions in a symmetrical and fluid-tight manner, under the action of the sphincter.

BRIEF DESCRIPTION OF THE DRAWINGS

The present invention is now described with reference to the attached drawings, in which:

FIG. 1 represents an endo-urethral prosthesis in accordance with a first embodiment of the invention;

FIG. 2 represents an anatomical section of the urinary tracts of the human male; a prosthesis according to FIG. 1 is represented in this section, in its implanted position;

FIGS. 3 and 4 are diagrammatic representations showing the cooperation of a prosthesis according to the invention and the striated muscular sphincter, respectively in the flow position with the sphincter relaxed, and in the closed position with the sphincter contracted;

FIG. 5 represents three variants, designated (a) through (c), of a flexible sleeve belonging to a prosthesis according to FIG. 1; each variant (a) through (c) is represented respectively in the flow position (miction) and in the closed position (continence) and in cross section;

FIG. 6 represents an endo-urethral prosthesis in accordance with a second embodiment of the invention;

FIG. 7 represents an endo-urethral prosthesis in accordance with a third embodiment of the invention;

FIG. 8 represents an assembly for insertion of a prosthesis according to FIG. 6, this assembly being shown at the top in FIG. 8b in the position in which it is detached from the prosthesis, and at the bottom in FIG. 8a in the position in which it is engaged on the prosthesis;

FIGS. 9 through 12 represent, respectively, four successive stages of the procedure for insertion of a prosthesis according to FIG. 6;

FIG. 13 represents a prosthesis in accordance with a final embodiment of the invention.

DESCRIPTION OF PREFERRED EMBODIMENTS

In accordance with FIG. 2, the urethra 1 extends upwards from the meatus urinarius 7 as far as the neck 3 of the bladder 2. Above the striated muscular sphincter 5, the urethra comprises a super-collicular prostatic segment 101 and a sub-collicular prostatic segment 102 on either side of the verumontanum. Below the sphincter 5, the urethra comprises, toward the meatus 7, the membranous segment 103, the bulbar segment 104, the perineal segment 105, and, finally, the penile segment 106.

A prosthesis 8 according to the invention, such as is represented in FIG. 1, is intended to be implanted, as will be described hereinafter, in the urethra 1 on either side of the sphincter 5.

Ex vivo, that is to say in its non-implanted state, as represented in FIG. 1, a prosthesis 8 according to the invention comprises two tubular elements 9 and 11, of cylindrical shape in the representation in FIG. 1, the wall of which consists of a relatively smooth and soft biocompatible and optionally biodegradable material, for example a silicone rubber. Each tubular element 9 or 11 is sufficiently flexible to conform to the segment of the urethra in which it is to be placed, while at the same time being sufficiently rigid to maintain an artificial endo-urethral passage. Each tubular element 9 or 11 has an external cross section which is substantially constant from one end to the other of said element. These two tubular elements are connected or attached to each other by a connection means which consists, according to the embodiments in FIGS. 1, 6, 7, and 13, of a flexible sleeve 10 which is intended to be held in the orifice of the sphincter 5, as shown, once implanted, in FIG. 2.

As is represented in FIG. 2, once put into place, as is described hereinafter, the prosthesis thus comprises, in a continuous manner, the two tubular elements 9 and 11 which are arranged in the urethra 1 on either side, respectively, of the sphincter 5 and are attached to each other via the flexible sleeve 10 which is held in the orifice of the sphincter 5.

As is shown in FIG. 1, the two ends of the flexible sleeve 10 are connected, in continuity of flow, to the two tubular elements 9 and 11, respectively. The wall of the sleeve 10 is more flexible, and in particular thinner, than the wall of each tubular element 9 or 11. In practice, this wall of the sleeve 10 can be made from a web of silicone, the tubular elements 9 and 11 for their part consisting of a wall of silicone rubber which is thicker by comparison. The join between the sleeve 10 on the one hand and the two tubular elements 9 and 11 is obtained in any suitable manner, for example by adhesive bonding. As is represented in FIG. 5, the flexible sleeve 10 can be open-worked about its circumference, in particular by longitudinal slots or windows, in such a way as to facilitate the bending of the sleeve 10 and to ensure continence; the dimensions of these windows or slots are such that the join between the tubular elements 9 and 11 is reduced to a bundle of strips or threads forming a continuation of said tubular elements 9 and 11.

As is shown diagrammatically in FIGS. 3 and 4, the wall of the flexible sleeve 10 is capable of assuming two configurations under the action of the striated muscular sphincter 5, namely a flow configuration represented in FIG. 3, having the shape of a cylinder, upon relaxation of the sphincter 5, and a closed configuration, represented in FIG. 4, corresponding to a biconical or hourglass shape, upon contraction of the sphincter 5.

As is represented in FIG. 3, but also in its ex vivo configuration, the tubular elements 9 and 11 form, together with the flexible sleeve 10, a conduit having an internal cross section which is substantially constant in the longitudinal direction of the prosthesis 8. Each tubular element 9 or 11 has an external profile which is substantially constant or uniform in the same longitudinal direction. Irrespective of the configuration, the two ends of the flexible sleeve 10 are connected in flow continuity to the two tubular elements 9 and 11, respectively. This being the case, it is possible, in a manner not shown, and when the caliber of the urethral meatus allows it, for the lower tubular element 11 to have an external cross section greater than that of the upper tubular element 9, for the purpose of promoting self-stabilizing and of preventing upward migration of the prosthesis.

As is represented in FIG. 1, ex vivo, that is to say free of any stress imposed by its implantation in the urethra, each tubular element 9 or 11 can have a predetermined and adapted angulation, along its axis, identical to or different than the natural or physiological angulation of the segment in which said tubular element is intended to be implanted. More specifically, taking into consideration the direction and orientation of implantation according to FIG. 2, the upper tubular segment 9 can have an angulation of between 140° and 160°, and preferably one equal to 150°, and the lower tubular segment 11 can have an angulation of between 110° and 130°, and preferably one equal to 120°. This angulation is remanent, which means that under stress it can be suppressed, but that, when there is no stress, each tubular element essentially recovers, in an elastic manner, its original angulation. The angulation used, for example that of the lower tubular element 11 in its part adjacent to the sleeve 10 facing the sphincter 5, can be chosen to contrast with the anatomical shape of the urethra, for example of the bulbar segment 104, and thus to counter the upward migration of the prosthesis through the sphincter 5.

The external diameter of the two tubular elements is about 7.3 mm (22 in accordance with the Charrière scale); it can be 8 mm (Charrière 24) for the lower tubular element.

As is shown in FIG. 1, the prosthesis 8 comprises a removal thread 14 at its lower end 15, still in the direction of implantation represented in FIG. 2.

In accordance with the embodiment represented in FIG. 13, each tubular element 9 or 11 can be open-worked with perforations 51 distributed along its length at the side near its free end, that is to say opposite the sleeve 10; these perforations promote the embedding of the prosthesis with respect to the urethral wall.

In accordance with the embodiment represented in FIG. 7, the upper tubular element 9 has one or more notches distributed along its length, for example a helical notch 9a, in the manner of a screw thread, or notches in a staggered arrangement, and this is again to promote the elimination of the natural secretions of the prostate or tissue debris freed by treatment thereof.

As is shown in FIG. 13, a metallic or non-metallic coil 52 constitutes a reinforcement for each tubular element 9 or 11. It is embedded in the elastomeric material of the tube of each tubular element, as is represented in FIG. 13, but it can also be externally exposed, for example for the purpose of therapeutic treatment of the urethral wall. The reinforcement 52 of each tubular element 9 or 11 extends from the sleeve 10 over only a part of the length of said tubular element, in such a way that the remaining part can be cut, for example in order to adapt the length of the tubular element 9 to that of the prostatic segment 101/102, or to adapt the length of the tubular element 11 with respect to the site of a stenosis in that portion of the urethra 1 below the sphincter 5.

As is shown in FIG. 13, the elastomeric material covers the metallic reinforcement 52, at least toward the outside, and thus constitutes at least the external part of each tubular element 9 or 11 in contact with the urethral wall.

In accordance with FIGS. 6 and 7, the upper end of the upper tubular element 9, that is to say the end opposite the connection sleeve 10, is closed transversely and is presented in the form of a convex and rounded stump 9b. This stump has one or two lateral orifices 9c for communicating with the inside of the tubular element 9.

Each tubular element 9 or 11 can be coated on its outer surface with a therapeutic substance for the purpose of treating the urethra.

In accordance with FIG. 8b, in order to insert a urethral prosthesis in accordance with FIG. 6 or FIG. 7, an assembly is used which comprises:

a semi-rigid and hollow mandrel 60 whose external cross section is adapted to receive the prosthesis 8 which is engaged onto it; this mandrel has, at one extremity, a conical outer limit stop 61, and, at the other extremity, a sealed end 62 against which the closed end 9b of the prosthesis 8 comes into abutment in its engaged position; this sealed end 62 of the mandrel 60 has an eyelet 62a for flow inside the mandrel 60, which eyelet 62a can be brought into line with the lateral orifice 9c of the prosthesis, again in its engaged position;

a rigid and hollow pusher 63 whose internal cross section is adapted for engagement of said pusher on the semi-rigid mandrel 60; the length of the pusher 63 is adapted to act, in its engaged position, as a spacer between the engaged prosthesis 8 and the outer limit stop 61 of the mandrel 60.

The insertion device previously described is used in the following manner.

A single component is formed from:

the mandrel 60;

the pusher 63, engaged on the mandrel 60, and coming into abutment against its proximal end, formed by the conical limit stop 61;

and, finally, the prosthesis 8 which is also engaged on the free end of the mandrel 60 so as to come into abutment via its end 9b against the free end 62 of the mandrel 60.

In this assembled position, represented at the bottom in FIG. 8a, the pusher 63 acts as a spacer between the prosthesis 8 and the outer limit stop 61 of the mandrel 60. The prosthesis 8 is oriented angularly with respect to the mandrel 60, in such a way that the flow eyelet 62a is in line with the lateral orifice 9c of the prosthesis, of greater cross section.

Following lubrication of the duct 1 of the urethra, the assembly which has been formed is inserted through the urethral meatus 7 until the upper end 9b of the prosthesis opens into the bladder 2. From this moment, the flow of urine through the mandrel 60 indicates that the insertion device has arrived in the bladder, in accordance with the position represented in FIG. 9.

The mandrel 60 is then released and withdrawn, while at the same time keeping the pusher 63 in position in the urethra in such a way that the prosthesis 8 does not move; compare FIG. 10.

Once the mandrel 60 has been withdrawn, the pusher 63 is itself withdrawn from the urethra 1; compare FIG. 11. At this stage, the lower tubular element 11 of the prosthesis 8 is situated level with the striated muscular sphincter.

A gentle downward pull, exerted via the thread 14, makes it possible to slide the lower tubular element 11 and to engage the flexible sleeve 10 in the sphincter.

At this moment, the operating surgeon immediately experiences a blocking effect on withdrawal, which corresponds to the correct positioning of the prosthesis 8 with respect to the sphincter 5 which closes on the flexible sleeve 10. The correct position of the prosthesis is thus found automatically; compare FIG. 12.

During this last operation, the operating surgeon can also use his/her index finger to perform rectal touch exploration since the lower tubular element 11 is clearly felt by the finger, and its passage this side of the sphincter 5 is clearly noted, with the disappearance of the firmness of said lower tubular element, replaced by the flexible sleeve 10. The correct positioning of the prosthesis 8 with respect to the sphincter 5 is completely painless, and it does not necessitate the use of any rigid instruments, for example forceps. Nor does it necessitate any radiological checks. At the very most, it may be facilitated by the use of an echography probe, which replaces the finger in the rectum.

From FIG. 12, the prosthesis in place can be easily withdrawn, using forceps for example, by simply pulling on the free edge of the lower tubular element 11; the resistance of the sphincter 5 is low since the closure pressure of the latter is less than the pressure exerted by a 100 cm water column. As the upper element 9 is engaged in the sphincter 5, the sliding and withdrawal of the prosthesis 8 are effected without them catching at all on the urethral wall.

A prosthesis in accordance with FIG. 6, put into place with an insertion device according to FIG. 8, is at one and the same time non-traumatic, positioned in a quasi-automatic manner with respect to the sphincter, and self-stabilizing.

This prosthesis is non-traumatic both by virtue of its external configuration and by virtue of its handling:

its configuration is non-traumatic on account of its convex or rounded, and optionally flexible, upper end 9b, which prevents any traumatism of the urethral mucosa, and thus any bleeding, on account of its virtually smooth external surface, that is to say without any specific roughening or reliefs, and on account of the flexible intermediate sleeve, permitting the normal action of the sphincter;

its handling is non-traumatic since, as has been described above, its positioning is as gentle and straightforward as that of an indwelling catheter; by permitting the normal functioning of the sphincter, the prosthesis is presented in the manner of an indwelling continence catheter; throughout the period during which the patient is provided with this prosthesis, the bladder is not injured, which fact prevents any formation of clots; and at the moment of its withdrawal, the prosthesis 8 slides out as a single piece without causing the patient any particular pain.

The positioning of a prosthesis according to the invention is quasi automatic since in the final analysis it is effected by means of simple tactile perception of a resistance at the moment when the sphincter closes on the flexible sleeve 10. According to the invention, the positioning is based on tactile locating, both by the traction exerted on the thread 14, and/or by a rectal touch exploration by which it is possible to detect the completion of the passage of the lower tubular element 11 through the sphincter 5. And, according to the invention, any error in positioning can be rectified by moving the prosthesis by means of a slight traction which causes the patient little pain and which for this reason does not necessitate general anesthesia.

And, finally, the prosthesis is self-stabilizing by virtue of the presence of the two tubular elements 9 and 11 on either side of the sphincter 5. This self-stabilizing can furthermore be improved by the presence of orifices or notches, as described in FIGS. 7 and 13, in which the urethral mucosa engages.

I claim:

1. A prosthesis adapted to be inserted and contained in a biological lumen or tract, comprising:

first and second tubular elements that are locatable on either side of a sphincter surrounding the lumen or tract, wherein the first and second tubular elements comprise at least a substantially smooth outer layer of a biocompatible material which is sufficiently flexible to conform to the lumen or tract and sufficiently rigid to maintain an artificial passage through the lumen or tract against a force that tends to obstruct the lumen or tract; and a connecting element comprising a first end that is connected to the first tubular element, a second end that is connected to the second tubular element, and a flexible middle portion joining the first and second ends that is locatable in the sphincter, wherein the middle portion can be moved by the sphincter to allow the sphincter to close naturally and thereby close the lumen or tract, and wherein abutment of the first and second tubular elements against the sphincter can substantially maintain position of the prosthesis in the lumen or tract.

2. The prosthesis according to claim 1, wherein the connecting element comprises a flexible sleeve.

3. The prosthesis according to claim 2, wherein the connecting element assumes a closed configuration upon contraction of the sphincter wherein fluid flow through the connecting element is prevented, and a flow configuration upon relaxation of the sphincter wherein fluid flow through the connecting element is possible.

4. The prosthesis according to claim 3, wherein the connecting element assumes an hourglass shape when in the closed configuration.

5. The prosthesis according to claim 3, wherein the connecting element assumes a cylindrical shape when in the flow configuration.

6. The prosthesis according to claim 3, wherein the first and second tubular elements and the connecting element form a conduit having a substantially constant inner diameter when the connecting element is in the flow configuration.

7. The prosthesis according to claim 1, wherein a thickness of a wall of the middle portion of the connecting element is smaller than a thickness of walls of the first and second tubular elements.

8. The prosthesis according to claim 1, wherein apertures are formed in at least the middle portion of the connecting element.

9. The prosthesis according to claim 1, wherein the connecting element comprises at least one strip of material, and wherein first and second ends of each at least one strip of material are connected to the first and second tubular elements, respectively.

10. The prosthesis according to claim 9, wherein the at least one strip of material comprises a thread.

11. The prosthesis according to claim 9, wherein the at least one strip of material comprises a plurality of strips of material, and wherein the plurality of strips of material are radially inwardly movable.

12. The prosthesis according to claim 1, wherein at least one of the first and second tubular elements includes a reinforcing element.

13. The prosthesis according to claim 12, wherein the reinforcing element comprises a coil of material embedded in a wall of the at least one tubular element.

14. The prosthesis according to claim 1, wherein a plurality of apertures are distributed along a length of at least one of the first and second tubular elements.

15. The prosthesis according to claim 1, wherein a plurality of undulations are distributed along an outer wall of at least one of the first and second tubular elements.

16. The prosthesis according to claim 1, wherein an end of at least one of the first and second tubular elements opposite the connecting element is closed and has a convex shape, and wherein at least one aperture is formed in a wall of the at least one tubular element adjacent the closed end.

17. The prosthesis according to claim 1, wherein a removal thread is attached to an end of at least one of the first and second tubular elements opposite the connecting element.

18. The prosthesis according to claim 1, wherein an external diameter of the first tubular element is greater than an external diameter of the second tubular element.

19. The prosthesis according to claim 1, wherein an external surface of at least one of the first and second tubular elements is coated with a therapeutic substance.

20. An assembly for treating a biological lumen or tract, comprising:

a prosthesis according to claim 16;

a semi-rigid cylindrical mandrel having a first end with an outer diameter that is adapted to pass inside an inner diameter of the prosthesis to engage the prosthesis, and wherein a second, opposite end of the mandrel has an outer limit stop; and a rigid and hollow cylindrical pusher having inner and outer diameters, the inner diameter allowing the mandrel to pass inside the pusher, wherein the pusher acts as a spacer between the engaged prosthesis and the outer limit stop.

21. An assembly according to claim 20, wherein the mandrel is hollow and includes an aperture that aligns with the at least one aperture adjacent the closed end of the prosthesis when the mandrel engages the prosthesis.

22. A method of treating an obstruction of a biological lumen or tract that passes through a sphincter using the prosthesis of claim 19, wherein the obstruction is due to an external force that tends to close the lumen or tract, and wherein the prosthesis is located in the biological lumen or tract such that the first and second tubular members are located on either side of the sphincter and the connecting element extends through the sphincter, comprising the steps of:

supporting an interior of the lumen or tract at the obstruction with a smooth walled portion of at least one of the first and second tubular elements so that the biological lumen or tract is open despite the external force that tends to close the lumen or tract; and allowing the sphincter to contract to block fluid flow through the lumen or tract, and to relax to permit fluid flow through the lumen or tract.

* * * * *